United States Patent [19]
Ambrosius et al.

[11] Patent Number: 5,965,424
[45] Date of Patent: Oct. 12, 1999

[54] METHODS FOR MAKING NEISSERIA OR HEMOPHILUS IGA PROTEASE AND DNA ENCODING THE PROTEASES

[75] Inventors: Dorothea Ambrosius, Iffeldorf; Carola Dony, Starnberg; Rainer Rudolph, Weilheim, all of Germany

[73] Assignee: Boehringer Mannheim GmbH, Mannheim-Waldhof, Germany

[21] Appl. No.: 08/210,535

[22] Filed: Mar. 18, 1994

Related U.S. Application Data

[63] Continuation-in-part of application No. 07/820,701, Jan. 10, 1992, abandoned.

[30] Foreign Application Priority Data

Jan. 11, 1991 [DE] Germany .............................. 41 00 704
Dec. 10, 1991 [DE] Germany .............................. 41 40 699

[51] Int. Cl.$^6$ .............................. C12N 9/52; C12N 15/57
[52] U.S. Cl. ...................... 435/221; 435/220; 435/172.3; 536/23.2
[58] Field of Search .................... 435/220, 221; 536/23.2

[56] References Cited

U.S. PATENT DOCUMENTS 4,620,948   11/1986   Builder et al. ........................... 530/419

FOREIGN PATENT DOCUMENTS 0254090      1/1987    European Pat. Off. .
0361475      4/1990    European Pat. Off. .
WO-A9011367  10/1990   WIPO .

OTHER PUBLICATIONS

Grundy et al., Journal of Bacteriology, vol. 169, No. 10, pp. 4442–4450, (Oct. 1987).
Bricker, Pro. of the Nat. Acad. of Sciences of USA, vol. 80 (May 1983).
Koomey, Prc. of the Nat. Acad. of Sci. of USA, vol. 79, No. 23, pp. 7881–7885 (1982).
Koronakis, EMBO J., vol. 8, No. 2, pp. 595–605 (1980).
Bowden, Biological Abstracts, vol. 265, No. 28, pp. 16760–16766. 1990.
Claassen, Journal of Bio. Chem., vol. 266, No. 17, (Jun. 1991).
Fishman, Chemical Abstracts. vol. 104, No. 15, p. 184 (Apr. 1986).
Pohlner et al. (1992) Biotechnology 10: 799–803.
Kadonaga et al. (1984) J. Biol. Chem. 259: 2149–2154.
Pohlner et al. (1987) Nature 325: 458–462.
Kane et al. (1988) TIBTECH 6: 95–100.
Klauser et al. (1990) EMBO J. 9: 1991–1999.
Loomes et al. (1990) Infect. Immun. 58: 1979–1985.
Poulsen et al. (1989) Infect Immum. 57: 3097–3105.
Gilbert et al. (1988) Infect Immun. 56: 1961–1966.
Pohlner et al. Bio/technology 10(799–803) 1992.
Kadonaga et al. J. Biol. Chem. 259: 2149–2154 (1984).
Pohlner et al. (1987) Nature 325: 458–462.
Kane et al. (1988) TIBTECH 6: 95–100.
Klauser et al. (1990) EMBO JOURNAL 9: 1991–1999.
Loomes, et al. (1990) Infect. Immun. 58: 1979–1985.
Poulsen et al. (1989) Infect. Immun. 57:3097–3105.
Gilbert et al. (1988) Infect. Immun. 56:1961–1966.

*Primary Examiner*—Robert A. Wax
*Assistant Examiner*—G. E. Bugaisky
*Attorney, Agent, or Firm*—Felfe & Lynch

[57] ABSTRACT

The present invention concerns a process for the isolation of recombinant IgA protease from inclusion bodies. In addition a recombinant DNA is claimed which codes for an IgA protease whose C-terminal helper sequence and preferably also its N-terminal signal sequence is no longer active.

15 Claims, No Drawings

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
         (A) LENGTH: 56 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:1:

GAAGAATTCG GAGGAAAAAT TAATGGCACT GGTACGTGAT GATGTCGATT ATCAAA          56

(2) INFORMATION FOR SEQ ID NO:2:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:2:

TTTTTGTAAT AAAGATCTTT GCCTTG          26

(2) INFORMATION FOR SEQ ID NO:3:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:3:

CAAGGCAAAG ATCTTTATTA CAAAAA          26

(2) INFORMATION FOR SEQ ID NO:4:

(i) SEQUENCE CHARACTERISTICS:
         (A) LENGTH: 44 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:4:

TTCAGCTGGT CGACTTATCA CGGGGCCGGC TTGACTGGGC GGCC          44

(2) INFORMATION FOR SEQ ID NO: 5:

(i) SEQUENCE CHARACTERISTICS:
         (A) LENGTH:  4899 base pairs
         (B) TYPE:  nucleic acid
         (C) STRANDEDNESS:  single
         (D) TOPOLOGY:  linear (ii) MOLECULE TYPE:  DNA (xi) SEQUENCE DESCRIPTION:  SEQ ID NO: 5:

```
GCAATAAAAC ACCAAAATGA ATGAGTTTAC ACAAAAAAAT ACTCAACACC ACCCAACCGG      60

CGTAAAATGC AAAACATTAT CGCTATTAAA ACGGTAAAAC CTTATGAAAG CCAAACGTTT     120

TAAAATTAAC GCCATATCCT TATCCATCTT TCTTGCCTAT GCCCTTACGC CATACTCAGA     180

AGCGGCATTG GTGAGAGACG ATGTCGATTA TCAAATATTC CGTGACTTTG CAGAAAACAA     240

AGGCAAATTT TTTGTCGGCG CAACCGATTT ATCAGTGAAA AACAAACGAG GTCAAACAT     300

CGGCAACGCA TTATCCAACG TACCGATGAT TGATTTTAGC GTTGCAGATG TCAACAAACG     360

CATAGCAACG GTAGTCGATC CCCAATATGC CGTCAGCGTC AAACACGCCA AGCAGAAGT     420

CCATACTTTT TATTACGGCC AATACAACGG TCATAATGAT GTAGCCGACA AAGAAAATGA     480

ATACCGCGTT GTCGAACAAA ATAACTATGA ACCCCATAAA GCTTGGGGTG CGAGCAATTT     540

AGGCCGCCTC GAAGATTATA ATATGGCGCG TTTTAATAAG TTTGTAACCG AAGTGGCACC     600

GATTGCACCA ACTGATGCCG GCGGCGGATT GGATACCTAC AAAGATAAAA ACCGTTTTTC     660

CTCTTTTGTC AGAATCGGTG CGGGCAGGCA ATTAGTTTAT GAAAAGGGGG TTTATCATCA     720

AGAAGGAAAT GAAAAAGGCT ACGATTTGCG CGATCTTTCA CAAGCCTATC GTTATGCCAT     780

TGCAGGTACG CCTTATAAAG ATATTAATAT TGACCAAACA ATGAATACCG AAGGTTTGAT     840

CGGCTTTGGT AATCATAATA AACAGTATTC GGCAGAAGAA CTTAAACAAG CACTTTCGCA     900

AGATGCGTTA ACAAATTACG GCGTGTTGGG CGATAGCGGC TCTCCACTAT TTGCTTTTGA     960

CAAACAAAAA AATCAATGGG TCTTTTTGGG AACTTACGAT TATTGGGCAG GTTACGGAAA    1020

AAAATCATGG CAAGAATGGA ATATCTATAA AAAAGAATTT GCAGATAAAA TCAAACAACA    1080

CGATAACGCC GGCACCGTCA AGGTAATGG AGAACATCAT TGGAAAACCA CGGGTACAAA    1140

CAGCCATATC GGTTCGACAG CGGTAAGGCT TGCCAACAAT GAAGGAGATG CGAACAACGG    1200

ACAAAATGTT ACCTTTGAAG ACAACGGCAC TTTGGTATTG AATCAAAACA TCAACCAAGG    1260

CGCGGGCGGC CTGTTTTTCA AAGGCGATTA CACAGTCAAA GGCGCAAATA ATGACATCAC    1320

TTGGTTAGGT GCGGGGATTG ATGTTGCCGA CGGCAAAAAA GTCGTTTGGC AAGTCAAAAA    1380

TCCGAATGGC GACAGATTGG CAAAAATCGG CAAAGGCACT TTGGAAATAA ACGGCACAGG    1440

CGTTAACCAA GGGCAATTAA AGGTCGGCGA CGGTACGGTT ATTCTGAATC AAAAAGCCGA    1500

TGCCGACAAA AAAGTTCAGG CTTTCTCCCA AGTCGGCATT GTCAGCGGAC GCGGTACATT    1560

GGTATTAAAT AGTTCAAATC AGATTAATCC CGATAACCTA TATTTCGGTT CCGTGGCGG    1620

TCGTTTGGAT GCCAATGGCA ATGACTTGAC TTTTGAACAC ATCCGCAACG TGGATGAAGG    1680

CGCGCGCATT GTCAACCACA ACACAGACCA CGCCTCCACA ATCACACTAA CGGGTAAATC    1740

TTTAATTACC AATCCGAACA GCCTTTCGGT ACATAGCATA CAAAATGACT ATGATGAAGA    1800

TGATTATAGT TATTATTACC GACCAAGGCG ACCCATCCCA CAAGGCAAAG ATCTTTATTA    1860

CAAAAACTAT CGTTATTACG CCCTAAAATC CGGCGGCAGG CTGAACGCAC CGATGCCCGA    1920

GAACGGTGTA GCAGAAAATA ACGACTGGAT CTTTATGGGA TATACGCAGG AGGAGGCCAG    1980

GAAAACGCG ATGAACCACA AAACAATCG GCGTATTGGC GATTTTGGCG GTTTCTTTGA    2040

CGAAGAAAAC GGAAAAGGAC ATAACGGCGC ATTAAACCTT AATTTCAATG GCAAAAGCGC    2100

GCAAAAGCGT TTCTTGTTAA CAGGCGGCGC CAATTTAAAC GGAAAAATAA GCGTAACTCA    2160

AGGCAATGTC TTGTTATCAG GTCGTCCAAC ACCACACGCA AGAGATTTTG TGAACAAATC    2220

TTCAGCCCGA AAAGACGCAC ATTTCTCCAA AAACAATGAA GTCGTATTTG AAGACGACTG    2280

GATAAACCGC ACATTCAAAG CCGCAGAAAT TGCGGTTAAC CAATCCGCAT CATTCTCTTC    2340

CGGAAGAAAT GTATCCGACA TCACCGCCAA CATCACCGCA ACAGACAACG CCAAAGTAAA    2400
```

```
TTTGGGTTAC AAAAACGGCG ATGAGGTTTG CGTGCGCTCG GACTATACCG GTTACGTTAC    2460

CTGCAACACA GGCAACTTAT CCGATAAGGC TTTAAACAGC TTTGATGCGA CACGGATTAA    2520

CGGCAATGTG AATTTGAATC AGAATGCGGC ATTGGTCTTG GGCAAGGCTG CATTATGGGG    2580

GAAAATTCAA GGACAAGGAA ACAGCCGTGT CAGCCTAAAC CAACATAGCA AATGGCATTT    2640

GACCGGCGAC AGCCAAGTAC ACAATCTGTC ATTGGCGGAT AGCCATATTC ATTTGAACAA    2700

CGCTTCCGAT GCGCAAAGTG CAAATAAATA CCACACGATC AAAATCAATC ATTTATCCGG    2760

TAACGGGCAT TTTCATTATC TGACGGACTT GGCGAAAAAT CTTGGGGATA AAGTGCTTGT    2820

GAAGGAATCC GCATCCGGCC ATTATCAGCT CCATGTTCAA AATAAAACAG GCGAACCTAA    2880

TCAGGAAGGG CTGGATCTCT TTGATGCATC ATCCGTACAA GACCGCTCCC GCCTTTTTGT    2940

TTCCTTGGCA AATCATTACG TCGATTTAGG CGCATTGCGT TATACAATCA AAACAGAAAA    3000

CGGTATTACC CGGTTGTACA ATCCTTATGC CGGGAACGGC CGCCCAGTCA AGCCGGCCCC    3060

GTCTCCTGCC GCAAACACGG CTTCTCAAGC ACAAAAGGCA ACACAAACGG ACGGTGCACA    3120

AATTGCCAAG CCTCAAAATA TCGTCGTCGC ACCGCCTAGC CCGCAGGCAA ATCAAGCCGA    3180

AGAAGCCCTC CGCCAACAAG CAAAAGCGGA GCAAGTGAAG CGTCAGCAAG CAGCAGAAGC    3240

AGAAAAAGTT GCACGTCAAA AAGACGAAGA GGCAAAACGC AAAGCAGCCG AAATTGCTCG    3300

TCAGCAGGAA GAAGCACGAA AAGCTGCAGA GTTAGCCGCC AAACAAAAGG CGGAAGCAGA    3360

GCGTAAAGCC AGAGAGTTGG CAAGACAAAA AGCAGAAGAG GCAAGTCATC AAGCTAATGC    3420

CAAACCAAAA CGTCGTAGAC GTCGGGCTAT ATTACCTAGA CCTCCTGCGC CAGTATTTTC    3480

ATTGGATGAT TATGATGCAA AAGACAATAG TGAATCATCA ATAGGTAATT TAGCTCGTGT    3540

AATACCTAGA ATGGGAAGGG AGTTAATTAA TGATTATGAA GAAATCCCCT TGGAGGAGTT    3600

GGAAGATGAA GCGGAAGAAG AACGTCGCCA AGCAACGCAA TTCCACTCCA AAAGTCGTAA    3660

CCGTAGAGCT ATATCATCGG AACCATCATC TGATGAAGAT GCATCTGAAT CGGTTTCCAC    3720

ATCAGACAAA CACCCTCAAG ATAATACGGA ACTTCATGAA AAAGTTGAGA CGGCGGGTTT    3780

ACAACCAAGA GCCGCGCAGC CGCGAACCCA AGCCGCCGCG CAAGCCGATG CAGTCAGCAC    3840

CAATACTAAC TCGGCTTTAT CTGACGCAAT GGCAAGCACG CAATCTATCT TGTTGGATAC    3900

AGGTGCTTAC TTAACACGGC ACATTGCACA AAAATCACGC GCTGATGCCG AAAAAAACAG    3960

TGTTTGGATG TCAAACACCG GTTATGGCCG TGATTATGCT TCCGCACAAT ATCGCCGGTT    4020

TAGTTCGAAA CGCACGCAAA CACAAATCGG CATTGACCGC AGCTTGTCCG AAAATATGCA    4080

GATAGGCGGA GTATTGACTT ACTCTGACAG TCAGCATACT TTTGATCAGG CGGGCGGCAA    4140

AAATACTTTT GTGCAAGCCA ACCTTTATGG TAAGTATTAT TTAAATGATG CTTGGTATGT    4200

GGCCGGCGAT ATTGGTGCGG GCAGCTTGAG AAGCCGGTTA CAAACGCAGC AAAAAGCAAA    4260

CTTTAACCGA ACAAGCATCC AAACCGGCCT TACTTTGGGC AATACGCTGA AAATCAATCA    4320

ATTCGAGATT GTCCCTAGTG CGGGTATCCG TTACAGCCGC CTGTCATCTG CAGATTACAA    4380

GTTGGGTGAC GACAGTGTTA AAGTAAGTTC TATGGCAGTG AAAACACTAA CGGCCGGACT    4440

GGATTTTGCT TATCGGTTTA AAGTCGGCAA CCTTACCGTA AAACCCTTGT TATCTGCAGC    4500

TTACTTTGCC AATTATGGCA AAGGCGGCGT GAATGTGGGC GGTAAATCCT TCGCCTATAA    4560

AGCAGATAAT CAACAGCAAT ATTCAGCAGG CGTCGCGTTA CTGTACCGTA ATGTTACATT    4620

AAACGTAAAT GGCAGTATTA CAAAAGGAAA ACAATTGGAA AAACAAAAAT CCGGACAAAT    4680

TAAAATACAG ATTCGTTTCT AAAATACCAA ATTCATAGCA AAATAAAATG CCGTCTGAAC    4740

TCAAGCTTCG GACGGCATTT TTATCAGACT AACAAAGCTA CAGCTCAATG CCTTTGAGTT    4800
```

-continued

```
TCGCCACGGT ATTGATGTCT TTGTCGCCGC GACCCGACAG GTTGACCAAA ATCACTTGGT    4860

CTTTACCCAT TTTCGGGCGC GTTTTATCGC CCGGACCAA                            4899
```

METHODS FOR MAKING NEISSERIA OR HEMOPHILUS IGA PROTEASE AND DNA ENCODING THE PROTEASES

This application is a continuation-in-part, of application Ser. No. 07/820,701, filed Jan. 10, 1992, now abandoned.

The present invention concerns a process for the production of method for making Neisseria or Haemophilus IgA proteases and DNA encoding the proteases from *E. coli* inclusion bodies.

Various pathogenic bacterial species (e.g. of the genus Neisseria, such as for example Neisseria gonorrhoeae and Neisseria meningitidis or the genus Haemophilus such as for example Haemophilus influenzae) which grow on human mucous membranes secrete proteases which are specific for human IgA1 and which are denoted IgA proteases. Immunoglobulin IgA1 is an important component of the secretory immune response that is intended to protect against infections by such pathogenic organisms (review: Kornfeld and Plaut, Ref.Infect.Dis. 3 (1981), 521–534). These proteolytic enzymes, which are as IgA proteases, cleave the following recognition sequences as described for example by Pohlner et al., (Nature 325 (1987), 458–462) SEQ ID NO:5

1. Pro-Ala-Pro→Ser-Pro
2. Pro-Pro→Ser-Pro
3. Pro-Pro→Ala-Pro
4. Pro-Pro→Thr-Pro

In this case "→" in each case denotes the cleavage site of the IgA protease.

The IgA proteases mentioned above are secretory proteins which have an N-terminal signal sequence for the transport into the periplasma and a C-terminal helper protein sequence which subsequently allows secretion from the periplasma into the medium.

The cloning and expression of an IgA protease from Neisseria in *E. coli* is described for example in PNAS USA 79 (1982) 7881–7885 and EMBO J. 3 (1984) 1595–1601.

It will be understood that the IgA proteases from the Neisseria and Haemophilus genera are particularly suitable in this application. Specifically, Neisseria gonorrhea, Neisseria meningitidis, and Haemophilus influenzae are examples of suitable sources of IgA proteases.

A disadvantage of the isolation of IgA protease according to the known methods is, however, the low productivity and vitality of the *E. coli* cells which have been transformed with an IgA protease gene which only results in a very low volume yield of IgA protease.

Since IgA protease is very important as a proteolytic enzyme for the cleavage of fusion proteins produced by genetic engineering (cf. WO91/11520) there is a great need for a method of isolating IgA protease which overcomes at least some of the drawbacks of the state of the art.

The object according to the present invention is achieved by a process for the production of recombinant IgA protease which is characterized in that (1) an IgA protease gene is modified in such a way that the DNA region of the IgA protease gene coding for the C-terminal helper sequence is no longer functionally active, (2) a host cell is transformed with the IgA protease gene modified according to step (1) or with a vector containing this modified gene, (3) the modified IgA protease gene is expressed in the transformed host cell, (4) the IgA protease which forms as inclusion bodies is isolated from the host cell and (5) the IgA protease is converted into active protein by in vitro activation.

It was surprisingly found that an IgA protease which no longer has a functionally active helper sequence (and thus can no longer be secreted from the host cell into the medium) is formed as inactive inclusion bodies within the host cell and that after activation of these inactive inclusion bodies very high volume yields of IgA protease are achieved. These inactive inclusion bodies can be isolated according to the usual methods from the cells and subsequently converted into the active form by means of in vitro activation.

It is essential for the process according to the present invention that the DNA region coding for the C-terminal helper sequence of the IgA protease is no longer functionally active. This can for example be achieved for example by partial or complete deletion of the DNA region coding for the helper sequence. The deletion of DNA fragments can be carried out in a manner familiar to one skilled in the art, as for example by in vitro mutagenesis on double-stranded or single-stranded DNA or by cleavage with suitable restriction enzymes and removal of restriction fragments from the region of the helper sequence. A further possibility for such a modification of the IgA protease gene is to carry out an in vitro mutagenesis in the DNA region coding for the helper sequence by means of which one or several translation stop codons are introduced into this region which then prevent a complete translation of the helper sequence when the IgA protease gene is expressed.

It is preferred in the process according to the present invention that the IgA protease gene is modified in such a way that the helper sequence of the IgA protease coded by this modified gene is completely deleted. This can for example be achieved by introducing one or several translation stop codons into the IgA protease gene directly at the beginning of the C-terminal helper sequence. A further possibility for the deletion of the helper sequence is a PCR reaction on IgA protease cDNA using suitable primers as described in example 1.

In the process according to the present invention it is also preferred that the IgA protease gene is also modified in such a way that the DNA region coding for the N-terminal signal sequence of the IgA protease is no longer functionally active. In this way the transport of the IgA protease into the periplasm is also blocked so that the inactive inclusion bodies are formed in the cytosol of the transformed host cell.

It is preferred that the inactivation of the signal sequence is carried out by completely deleting the corresponding DNA region according to the usual techniques. Subsequently DNA sequences from the DNA regions coding for the mature protein which may have been lost can be filled in again by introducing a synthetic oligonucleotide by genetic engineering. The signal sequence can, however, also be deleted by a PCR reaction using suitable primers as described in example 1.

A prokaryotic cell, especially an *E. coli* cell, is preferably used as the host cell for the process according to the present invention. In addition it is preferred that the host cell is transformed with a DNA sequence coding for an IgA protease which is under the control of an inducible promoter. Examples of suitable inducible promoters are the tac, lac or trp promoter or other similar promoters which are known to one skilled in the area of molecular biology.

The IgA protease produced in the process according to the present invention is formed in the host cell as inclusion bodies. The isolation of inclusion bodies and their conversion into active protein by in vitro activation can be carried out in any manner known to one skilled in the art. Examples of such methods are described for example in EP-A 0 361 475, DE-A 36 11 817, DE-A 35 37 708, WO 87/02673; Jaenicke, R. & Rudolph, R. (1989) Protein structure—a practical approach, Ed.: Creighton T.E. Oxford University Press, 191; Rudolph, R. (1990) Modern methods in protein and nucleic acid analysis, Ed.: Tschesche, published by H. Walter deGruyter, 149–171; Jaenicke, R. (1987) Prog. Biophys. Molec. Biol. 49, 117.

The in vitro activation of the IgA protease preferably includes a solubilization step and a renaturation step. The renaturation step in this process can be carried out by feeding the denatured protein continuously or discontinuously into the renaturation buffer. In this process it is preferred that the renaturation step is carried out in the form of discontinuous pulse renaturation.

It is particularly preferred that the renaturation step for the activation of the IgA protease is carried out in the presence of 0.2 to 1 mol/l arginine and most preferably of 0.4 to 0.8 mol/l arginine. In addition it is preferred that the reactivation is carried out at a pH of 5 to 9, especially at a pH of 6 to 8.

When the IgA protease is renatured from inactive inclusion bodies, active soluble protein is formed in a yield which ranges from about 10% to over 30%, depending on the starting material and renaturation method. Although the renaturation yield is not quantitative, nevertheless a substantially higher yield of active IgA protease is obtained with the process according to the present invention compared to conventional methods.

The present invention also concerns an IgA protease which has been produced by a process according to the present invention i.e. by activation from inclusion bodies.

In addition the invention concerns a recombinant DNA which codes for an IgA protease and is modified in such a way that upon expression of the recombinant DNA an IgA protease results whose C-terminal helper sequence is no longer functionally active and is preferably even completely deleted. The recombinant DNA according to the present invention is preferably also modified in such a way that upon expression of the recombinant DNA an IgA protease is formed whose N-terminal signal sequence is no longer functionally active and preferably is completely deleted. Genetic engineering methods for the modification or deletion of DNA regions which lead to the desired results have already been mentioned or are so familiar to one skilled in the area of molecular biology that they do not have to be explicitly elucidated.

The present invention also concerns a recombinant vector which contains at least one copy of a recombinant DNA according to the present invention. The recombinant DNA according to the present invention in this vector is preferably under the control of an inducible promoter. The vector according to the present invention can be present outside the chromosome of the host cell (e.g. a plasmid) or integrated in the genome of the host cell (e.g. bacteriophage in an E. coli cell). The vector is preferably a plasmid.

The invention in addition concerns a cell which is transformed with a recombinant DNA according to the present invention or with a recombinant vector according to the present invention. This cell is preferably a prokaryotic cell and particularly preferably an E. coli cell.

The invention is further elucidated in the following by the present examples in conjunction with the sequence protocols.

| | |
|---|---|
| SEQ. ID. NO. 1 | shows the primer A used in example 1 |
| SEQ. ID. NO. 2 | shows the primer B |
| SEQ. ID. NO. 3 | shows the primer C |
| SEQ. ID. NO. 4 | shows the primer D |

The plasmid pMAC 1 was deposited at the German Collection for Microorganisms (DSM), Griesebachstraβe 8, D-3400 Göttingen and assigned the number DSM 6261.

EXAMPLE 1

Preparation of plasmid constructs for the expression of IgA protease in the form of inclusion bodies In order to express IgA protease as inclusion bodies, the region coding for the protein without signal sequence and helper sequence is cloned downstream of a strong promoter as described in the following (amino acid position+1 to position 959, Pohlner J., Halter R., Beyreuther K., Meyer T. F., Nature 325, (1987), 458–462).

It will be understood that the signal and helper sequences are described as a) those sequence regions of the IgA protease gene from N. gonorrhea, as defined in SEQ ID NO. 5 of this application, b) those sequences which correspond to the sequences recited in (a) within the scope of degeneracy of the genetic code, or (c) sequences hybridizing with the sequences of (a) or (b) under stringent conditions.

Stringent hybridization conditions are those conditions described in J. Sambrook, Molecular Cloning, Laboratory Manual (1989) 2nd Edition, Cold Spring Harbor, Laboratory Press, New York (see pp. 9.47–9.55), the contents of which are incorporated herein in their entirety. The washing step following the hybridization shall take place in 0.1× SSC and 0.5% SDS, preferably at a temperature of 55° C., especially preferably at 60° C., and most preferably at 68° C.

For this chromosomal DNA is isolated from N. gonorrhoeae (e.g. MS 11) and used to carry out a polymerase chain reaction (PCR, method cf. EP-A 0 200 362, EP-A 0 201 184). The following primers are used for the PCR.

Primer A (SEQ. ID. NO. 1):

```
5' GAAGAATTCGGAGGAAAAATTAATGGCACTGGTACGTGATGATGTCGATTATCAAA 3'
```

Primer B (SEQ. ID. NO. 2):

```
5' TTTTTGTAATAAAGATCTTTGCCTTG 3'
```

The first 5 codons of the IgA protease were optimized for efficient expression in E. coli without changing the amino acid sequence and used for primer A, which includes the ATG start codon as well as an Eco RI recognition sequence (GAATTC).

Primer B contains sequences adjacent to the Bgl II recognition sequence of the IgA protease (ca. amino acid positions 553–561). The PCR fragment (A/B=ca. 1650 bp, 5' terminal region of the IgA protease gene) obtained in this way is purified and recleaved with the enzymes ECo RI/Bgl II.

In order to prepare the 3' region of the IgA protease gene a second PCR reaction is carried out with the following primers:

Primer C (SEQ. ID. NO. 3):

5' CAAGGCAAAGATCTTTATTACAAAAA 3'

Primer D (SEQ. ID. NO. 4):

5' TTCAGCTGGTCGACTTATCACGGGGCCGGCTTGACTGGGCGGCC 3'

Primer C corresponds to the coding region of primer B (Bgl II cleavage site) and primer D contains sequences of amino acid positions 952–959 with an adjacent stop codon and a Sal I recognition sequence. The PCR fragment (C/D= 1200 bp) obtained in this way is isolated and recleaved with the enzymes Bgl II/Sal I.

Subsequently a three fragment ligation is carried out: with the fragments A/B, the fragment C/D and the vector pKK 223-3 (DSM 3694P) which was previously digested with the enzymes Eco RI and Sal I and purified. The vector obtained in this way is denoted IgA-Prot III and is transformed in *E. coli* K12.

EXAMPLE 2

(Comparative Example)
Isolation of soluble IgA protease according to the conventional method.

a) Isolation from 1 l shaking culture

*E. coli* K12 cells transformed with the plasmid pMAC1 (8878 bp) were used as the starting material. The complete coding region for IgA protease is located on this plasmid and is under the control of the lambda promoter. The plasmid carries ampicillin resistance.

The cells were cultured in LB medium overnight at 28° C. and subsequently diluted 1:100 with LB medium. The culture was then incubated for a further 4 hours at 37° C. The cells were separated by a centrifugation step. The culture supernatant was sterile-filtered over a cellulose-acetate filter, dialyzed against 20 mmol/l Tris/HCl, pH 7.5, 10 mmol/l EDTA, 10% glycerol (buffer A) and concentrated to 1/10 its volume with the aid of a SALVIA capillary dialyser E-15U.

Negative elution on DEAE-Sephadex A-50 in 20 mmol/l Tris/HCl, pH 7.5, 10 mmol/l EDTA and 10% glycerol was carried out as the first purification step. The column was loaded with 0.5 mg protein per 1 ml gel matrix. In this separation the IgA protease is in the eluant and most of the *E. coli* proteins are bound to the carrier.

Washing the column matrix again with buffer A plus 1 mol/l NaCl showed that less than 10% of the IgA protease binds to the column material.

Finally it is purified on a cation exchanger (Fractogel$^R$-EMD-SO$_3^-$-650M). The protein binds in 20 mmol/l Tris/HCl, 10 mmol/l EDTA, 10% glycerol pH 7.0. Then the buffer can be changed to pH 8.0. The elution is carried out with a linearly increasing NaCl gradient whereby the IgA protease is eluted with a buffer of pH 8.0 at a salt concentration of 0.1 mol/l NaCl and with a buffer of pH 7.0 at 0.2 mol/l NaCl.

| Result: | |
|---|---|
| Concentrate before DEAE-Sephadex | 3.5 mg protease (70% pure) |
| Eluate after DEAE-Sephadex | 2.4 mg protease (90% pure) |
| Eluate after Fractogel$^R$-EMD-SO$_3^-$-650M | 1 mg protease (≧95% purity) | b) Isolation of IgA protease from a 10 l fermenter

The starting material and purification were carried out analogously to example 2a).

| Result: | |
|---|---|
| Concentrate before DEAE-Sephadex: | 50 mg IgA protease (50% purity) |
| Eluate after DEAE-Sephadex: | 30 mg IgA protease (60% purity) |
| Eluate after Fractogel$^R$-EMD-SO$_3^-$-650M: | 12 mg IgA protease (≧95% purity) |

EXAMPLE 3

Isolation of IgA protease from inclusion bodies (process according to the present invention)

The starting material was the construct IgA-Prot III (example 1) in *E. coli* cells (DSM 3689) which additionally contain a lacI$^q$ plasmid for the expression of the lac repressor.

500 ml LB medium containing 50 μg/ml kanamycin and 50 μg/ml ampicillin was prepared for the 1 l fermentation culture. This medium was inoculated with 7.5 ml of an overnight culture which resulted in an OD$_{550}$ of ca. 0.1. Then a 3 to 4 hour incubation at 37° C. was carried out while shaking (150 rpm). The cells were induced with 5 mmol/l IPTG at an OD$_{550}$ of ca. 0.8. The cells were harvested after a 4 hour incubation at 37° C. while shaking (150 rpm).

IB preparation:

The cells are harvested by centrifugation, taken up in 10 ml Tris-magnesium buffer (10 mmol/l Tris, pH 8.0, 1 mmol/l Mgcl$_2$) and lysed with lysozyme (0.3 mg/ml).

They are incubated for 15 minutes at 37° C. and subjected to one passage of a French press (1200 psi). Subsequently DNAse digestion (1 mg DNAse I) is carried out for 30 minutes at 370° C. 20 ml 0.5 mol/l NaCl, 20 mmol/l EDTA, pH 8.0 and 3 ml 20% Triton X100 is added and incubated for 10 minutes at room temperature.

The suspension is centrifuged for 10 minutes at 15000 rpm and 4° C. The pellet is taken up in 30 ml 50 mmol/l TRIS, pH 8.0, 50 mmol/l EDTA and 0.5% Triton X100 and treated with ultrasound. It is centrifuged again, resuspended and treated with ultrasound. This procedure is repeated an additional two times. Subsequently it is centrifuged and the pellets obtained in this way are used as IBs in example 3.

Table 1 shows the results for the fermentation in a 1 l shaking culture and in a 10 l fermenter.

TABLE 1

| Fermentation | *E. coli* strain | Total protein from IB material (g) | IgA protease (%) | IgA protease (g) |
|---|---|---|---|---|
| 1 l | HB 101 | 0.125 | 50–70 | 0.06–0.09 |
| 10 l | K12 C600 | 20.8 | 30–50 | 6.2–10.4 |

It can be seen from Table 1 that 60–90 mg protease is obtained as inclusion body (IB) material from the 1 l shaking culture. At a renaturation yield of ca. 10% this would yield 6 to 9 mg active IgA protease (compared to 3.5 mg by the conventional method).

6.2 to 10.4 g protease is obtained as IB material from the 10 l fermenter. This would yield 620 to 1040 mg IgA protease if 10% is renatured (compared to 50 mg protease by the conventional method).

It can be clearly seen from these results that the process according to the present invention results in an increase in the yield of at least 2 to 3-fold (1 l culture) or 20 to 30-fold (10 l fermenter).

EXAMPLE 4

Renaturation of the IgA protease from inclusion bodies (1 l fermentation)

The inclusion bodies were first solubilized, then dialyzed and then renatured in the respective buffers.

Solublization of the IB material:
6 mol/l guanidine/HCl, pH 8.5
0.1 mol/l Tris
1 mmol/l EDTA
0.1 mol/l dithioerythreitol (DTE)
Incubation: 2 h at room temperature
Vol: 10 ml, protein concentration:10 mg/ml
Dialysis of the solution:
6 mol/l guanidine/HCl, pH 3
1 mmol/l EDTA
Duration: 12 h at room temperature
against 10 l buffer
Renaturation buffer:
1) 100 mmol/l Tris, 1 mmol/l EDTA, 1 mmol/l DTE, pH 8.5
2) 100 mmol/l Tris, 1 mmol/l EDTA, 1 mmol/l DTE, pH 7.5
3) 20 mmol/l Tris, 1 mmol/l EDTA, 1 mmol/l DTE, pH 8.0
4) 0.6 mol/l Arg/HCl, 1 mmol/l EDTA, 1 mmol/l DTE, pH 8.0
5) 0.6 mol/l Arg/HCl, 1 mmol/l EDTA, 5 mmol/l reduced glutathione (GSH)/0.5 mmol/l oxidized glutathione (GSSG), pH 8

Pulse renaturation:

The denatured protein is added in 5 portions to the renaturation buffer; the time interval between the individual additions was 30 minutes and the protein concentration in the preparation increased by 20 μg/ml per pulse. The final protein concentration was eventually 100 μg/ml.

In order to determine the activity of the renatured IgA protease a dialysis is carried out in cleavage buffer (50 mmol/l Tris/HCl pH 8, 1 mmol/l CaCl$_2$). Human IgA was used as the cleavage substrate. Table 2 shows the results of the cleavage experiments (incubation: 6 h at 37° C.) on the renaturates obtained by using the above renaturation buffers (1–5).

TABLE 2

Cleavage of human IgA with IgA protease isolated according to the present example (incubation: 6 h at 37° C.). The isolate obtained after the dialysis contains about 50% IgA protease.

| Renaturate | Ratio protease/substrate (μg) | Cleavage (%) |
|---|---|---|
| 1 | 1:20 | 10 |
| 2 | 1:20 | 30 |
| 3 | 1:20 | 10 |
| 4/5 | 1:100 | 100 |
|  | 1:500 | 50 |
|  | 1:1000 | 30 |
|  | 1:2000 | 10 |
|  | 1:5000 | 5 |
| soluble protease (100% pure) | 1:500 | 100 |

It can be seen in Table 2 that IgA protease can be renatured in all buffers. The yields in an arginine (Arg) buffer are, however, 10 to 100-fold higher than without arginine. As a comparison the substrate was cleaved by 100% with soluble purified IgA protease (according to example 1) at a protease:substrate ratio of 1:500. From this a renaturation yield of ca. 50% can be determined for buffer 4) and 5).

EXAMPLE 5

Dependence of the optimization of the renaturation of IgA protease from inclusion bodies on the pH and arginine concentration solubilization and dialysis are analogous to example 4.

Pulse renaturation: protein addition was carried out as ed in example 4.

1) Determination of the renaturation yield while varying the pH value.
   0.6 mol/l Arg/HCl
   1 mmol/l EDTA
   pH 4, 6, 8
2) Renaturation while varying the arginine concentration
   1 mmol/l EDTA, pH 8
   1 mmol/l DTE
   Arg/HCl: 0.2; 0.4; 0.6 and 0.8 mol/l Subseqently dialysis was carried out at room temperature against a 100-fold volume of the cleavage buffer (50 mmol/l Tris/HCl, pH 8, 1 mmol/l CaCl$_2$).

TABLE 3

Cleavaqe of human IgA with the aid of the IgA protease isolated accordinq to the present example. The dialysate contains about 50 to 70% IgA protease. In the cleavage preparation 50 μg substrate was incubated with 1 μg renatured IgA protease for 6 h at 37° C.

| pH | % Cleavage | Arginine (mol/l) | % Cleavage |
|---|---|---|---|
| 4 | 10 | 0.2 | 85 |
| 6 | 95 | 0.4 | 90 |
| 8 | 100 | 0.6 | 95 |
|  |  | 0.8 | 95 |

The optimal reactivation of the IgA protease is at a pH of 6 to 8 and at an arginine concentration of 0.6 to 0.8 mol/l.

We claim:

1. The method for producing a recombinant Neisseria or Haemophilus IgA protease, comprising:
   (a) modifying a gene which codes for a Neisseria or Haemophilus IgA protein to inactivate a C-terminal helper sequence of said Neisseria or Haemophilus IgA protease,
   (b) transforming a prokaryotic host cell with a DNA molecule which comprises the modified gene of (a),
   (c) culturing the prokaryotic host cell transformed in (b) to express recombinant Neisseria or Haemophilus IgA protease as inclusion bodies,
   (d) isolating inclusion bodes formed in (c), and
   (e) converting isolated inclusion bodies into active Neisseria or Haemophilus IgA protease.

2. The method of claim 1, comprising modifying said gene which codes for IgA protease by deleting at least a portion of the DNA sequence coding for said C-terminal helper sequence.

3. The method of claim 1, comprising modifying said gene which codes for IgA protease by introducing at least one stop codon into the region of said gene which codes for said C-terminal helper sequence.

4. The method of claim 1, further comprising modifying said gene which codes for IgA protease to inactive the N-terminal signal sequence of said IgA protease.

5. The method of claim 4, comprising inactivating said N-terminal signal sequence by deleting the sequence of said gene which codes for it.

6. The method of claim 1, wherein said host cell is a prokaryote.

7. The method of claim 6, wherein said prokaryote is *E. coli*.

8. The method of claim 1, wherein said DNA sequence further comprises an inducible promoter.

9. The method of claim 1, comprising activating said IgA protease by solubilizing and renaturing said inclusion body.

10. The method of claim 9, wherein said renaturing comprises pulse renaturing.

11. The method of claim 9, comprising renaturing said inclusion body in the presence of from 0.2 to 1.0 mol/l of arginine.

12. The method of claim 11, wherein said arginine is present at a concentration of from 0.4 to 0.8 mol/l.

13. The method of claim 9, comprising renaturing said inclusion body at a pH of from 6–8.

14. An isolated DNA molecule which codes for a Neisseria or Haemophilus IgA protease which has an inactive C-terminal helper sequence and an inactive N-terminal signal sequence.

15. An isolated DNA molecule which codes for a Neisseria or Haemophilus IgA protease which lacks both a C-terminal helper sequence and an N-terminal helper sequence.

* * * * *